United States Patent [19]

Wight et al.

[11] 4,110,444

[45] Aug. 29, 1978

[54] THIOCARBAMATES

[75] Inventors: Hewitt G. Wight; Tracey G. Call, both of San Luis Obispo; Marvin L. Mortensen, Altascadero, all of Calif.

[73] Assignee: The California Polytechnic State University Foundation, San Luis Obispo, Calif.

[21] Appl. No.: 773,064

[22] Filed: Feb. 28, 1977

Related U.S. Application Data

[63] Continuation-in-part of Ser. No. 579,449, May 21, 1975, abandoned.

[51] Int. Cl.² ................... A61K 31/655; C09B 25/00
[52] U.S. Cl. ................... 424/226; 260/207.1
[58] Field of Search ................... 260/207.1; 424/226

[56] References Cited

U.S. PATENT DOCUMENTS 3,097,198  7/1963  Fishwick et al. ................... 260/207.1

Primary Examiner—Frederick E. Waddell

[57] ABSTRACT

The disclosure is directed to mono- and dithiocarbamates (hereinafter thiocarbamates) corresponding to the formula RNHCXSR'COOR'' wherein R is paraphenylazophenyl or metafluorophenyl, X is oxygen when R is paraphenylazophenyl and X is sulfur when R is metafluorophenyl, R' is an alkylene radical having generally from 1 to about 5 carbon atoms and R'' is hydrogen or an alkyl radical having generally from 1 to about 10 carbon atoms. The thiocarbamates, in acid form, can be prepared by blocking the carboxyl group of a mercaptoalkanoic acid with a carboxyl blocking agent; interacting the carboxyl blocked, mercaptoalkanoic acid with paraphenylazophenyl isocyanate or metafluorophenyl isothiocyanate to produce a thiocarbamate reaction product; and treating the thiocarbamate reaction product to remove the carboxyl blocking agent and to obtain the product in carboxylic acid form. The thiocarbamates, in ester form, can be prepared by interacting an alkyl mercaptoalkanoate with paraphenylazophenyl isocyanate or metafluorophenyl isothiocyanate. The thiocarbamates possess the unique property of being able to modify and enhance the strength of biological membranes.

34 Claims, No Drawings

THIOCARBAMATES

CROSS-REFERENCE TO RELATED APPLICATION

This application is a continuation in part of U.S. Pat. Application No. 579,449 filed on May 21, 1975 (now abandoned).

SUMMARY OF THE INVENTION

This invention relates to thiocarbamate compositions, a method for preparing the same, and the use thereof to modify biological membranes.

The term "thiocarbamate(s)" as used in the specification and claims refers to and identifies mono- and dithiocarbamates as defined herein.

In accordance with this invention, it has been unexpectedly discovered that certain thiocarbamates possess the unique property of being able to enhance the strength of biological membranes. In particular, it has been found that erythrocytes of mammals treated with these thiocarbamates have increased resistance to hemolysis and, thus, these thiocarbamates are useful in treating disorders of erythrocyte membranes as in hemolytic anemia.

The thiocarbamates which possess this unique property correspond to the formula:

RNHCXSR'COOR" wherein
- R is paraphenylazophenyl or metafluorophenyl,
- X is oxygen when R is paraphenylazophenyl and X is sulfur when R is metafluorophenyl,
- R' is an alkylene radical, and
- R" is hydrogen or an alkyl radical.

The thiocarbamates, in acid form, are prepared by: (a) blocking the carboxyl group of a mercaptoalkanoic acid with a carboxyl blocking agent; (b) interacting the carboxyl blocked, mercaptoalkanoic acid with paraphenylazophenyl isocyanate or metafluorophenyl isothiocyanate to produce a thiocarbamate reaction product; and (c) treating the thiocarbamate reaction product to remove the carboxyl blocking agent and to obtain the product in carboxylic acid form.

The thiocarbamates, in ester form, are prepared by interacting an alkyl mercaptoalkanoate with paraphenylazophenylisocyanate or metafluorophenyl isothiocyanate.

DETAILED DESCRIPTION

The thiocarbamates of this invention have the following structural formula:

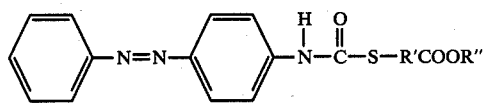

and

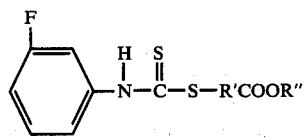

wherein R' is an alkylene radical generally having from 1 to about 5 carbon atoms, and, preferably having from 1 to about 2 carbon atoms; and R" is hydrogen or an alkyl radical generally having from 1 to about 10 carbon atoms and, preferably, having from 1 to about 5 carbon atoms.

The following compounds are illustrative of the thiocarbamate compositions of this invention:

2-(N-paraphenylazophenylthiocarbamoyl)-ethanoic acid.
2-(N-paraphenylazophenylthiocarbamoyl)-propanoic acid.
3-(N-paraphenylazophenylthiocarbamoyl)-propanoic acid.
4-(N-paraphenylazophenylthiocarbamoyl)-butanoic acid.
5-(N-paraphenylazophenylthiocarbamoyl)-pentanoic acid.
6-(N-paraphenylazophenylthiocarbamoyl)-hexanoic acid.
Methyl 3-(N-paraphenylazophenylthiocarbamoyl)-propanoate.
Ethyl 3-(N-paraphenylazophenylthiocarbamoyl)-propanoate.
Propyl 3-(N-paraphenylazophenylthiocarbamoyl)-propanoate.
Butyl 3-(N-paraphenylazophenylthiocarbamoyl)-propanoate.
Heptyl 3-(N-paraphenylazophenylthiocarbamoyl)-propanoate.
Octyl 3-(N-paraphenylazophenylthiocarbamoyl)-propanoate.
Decyl 3-(N-paraphenylazophenylthiocarbamoyl)-propanoate.
2-(N-metafluorophenyldithiocarbamoyl)-ethanoic acid.
3-(N-metafluorophenyldithiocarbamoyl)-propanoic acid.
4-(N-metafluorophenyldithiocarbamoyl)-butanoic acid.
5-(N-metafluorophenyldithiocarbamoyl)-pentanoic acid.
6-(N-metafluorophenyldithiocarbamoyl)-hexanoic acid.
Methyl 3-(N-metafluorophenyldithiocarbamoyl)-propanoate.
Ethyl 3-(N-metafluorophenyldithiocarbamoyl)-propanoate.
Butyl 3-(N-metafluorophenyldithiocarbamoyl)-propanoate.
Heptyl 3-(N-metafluorophenyldithiocarbamoyl)-propanoate.
Octyl 3-(N-metafluorophenyldithiocarbamoyl)-propanoate.
Decyl 3-(N-metafluorophenyldithiocarbamoyl)-propanoate.
2-(N-metafluorophenyldithiocarbamoyl)-propanoic acid.

The thiocarbamates, in acid form, are prepared by initially blocking the carboxyl group of a mercaptoalkanoic acid with an organic base, interacting the carboxyl blocked, mercaptoalkanoic acid with paraphenylazophenyl isocyanate or metafluorophenyldithio isocyanate to produce a thiocarbamate reaction product and treating the thiocarbamate reaction product to remove the carboxyl blocking agent and to obtain the product in carboxylic acid form.

In the initial step of the process, the carboxyl group of the mercaptoalkanoic acid is blocked by interacting the mercaptoalkanoic acid with an organic base in an inert organic solvent to form a carboxylate linkage.

The mercaptoalkanoic acids which can be used to prepare the thiocarbamates of this invention include, by way of example, the following compounds: 2-mercaptoethanoic acid, 2-mercaptopropanoic acid, 3-mercaptopropanoic acid, 4-mercaptobutanoic acid, 5-mercaptopentanoic acid and 6-mercaptohexanoic acid.

The particular blocking agent which is employed is not critical and any suitable organic base can be utilized as long as it is organophilic, i.e., soluble in the inert organic solvent, and can be readily removed from the carboxyl group by a more basic, water soluble base following the principal reaction step. Suitable carboxyl blocking agents include tertiary amines having up to about 10 carbon atoms. The organo portion of the amine can be linear, cyclic or both. An organic amine which has been found to be particularly effective as a blocking agent is triethylamine.

The carboxyl blocking step is carried out in an inert organic solvent. Since the choice of solvent is not critical, any suitable solvent may be used such as benzene, toluene, xylene and the like. In a preferred aspect, the mercaptoalkanoic acid and the organic base are reacted in the solvent, in about equal molar ratios, under agitation conditions and at ambient temperature and pressure.

To the solvent solution of the carboxyl blocked, mercaptoalkanoic acid, there is added, with agitation, an aryl isocyanate and, particularly, paraphenylazophenyl or metafluorophenyl isocyanate, in about an equal molar ratio with respect to the carboxyl blocked, mercaptoalkanoic acid, to produce an aryl thiocarbamate reaction product. When the carboxyl blocked, mercaptoalkanoic acid is triethylammonium 3-mercaptopropanoate and the isocyanate is paraphenylazophenyl isocyanate, then the reaction product is triethylammonium 3-(N-paraphenylazophenylthiocarbamoyl)-propanoate.

To the solvent solution of the carboxyl blocked, thiocarbamate reaction product, there is added an aqueous solution of a water soluble base, more basic than the carboxyl blocking agent, to displace the blocking agent from the reaction product and to form the salt of the reaction product with the cation of the water soluble base. The water soluble bases which may be utilized to displace the carboxyl blocking agent include, for example, alkali metal hydroxides, alkali metal carbonates and alkali metal bicarbonates as well as other hydroxides, carbonates and bicarbonates. The preferred water soluble bases are sodium and potassium bicarbonates. The solution concentration of the water soluble base and, in particular, the solution concentration for sodium or potassium hydroxide should not exceed about 0.10 N in order to prevent decomposition of the product. The volume of the water soluble base which is used is such as to provide at least about an equivalent amount of base to displace the blocking agent from the thiocarbamate reaction product.

The salt resulting from the addition of the water soluble base to the carboxyl blocked, thiocarbamate reaction product is preferentially soluble in the aqueous medium with the latter being immiscible in the solvent. The aqueous medium and the solvent resolve themselves into separate fluid layers and the aqueous layer containing the salt is separated from the solvent.

A converting acid is added to the aqueous solution of the salt to obtain the thiocarbamate reaction product in carboxylic acid form. Any suitable converting acid may be used for this purpose. An effective acid is hydrochloric acid. The amount of acid which is used is such as to provide at least an equivalent amount thereof to displace the cation from the salt and convert the same to the carboxylic acid form.

Water alone can be used to extract the carboxyl blocked, thiocarbamate reaction product from the solvent solution thereof. The water solution of the reaction product is treated with a converting acid to obtain the product in carboxylic acid form.

The thiocarbamate, in carboxylic acid form, is a crystalline product which can be separated from the aqueous medium by filtration. The crude product can be purified by dissolving it in and recrystallizing it from a recrystallizing solvent such as an acetone-benzene system.

The thiocarbamates, in ester form, are prepared by interacting an alkyl mercaptoalkanoate with paraphenylazophenyl isocyanate or metafluorophenyl isothiocyanate, in about equal molar ratios, in an inert organic solvent.

The alkyl mercaptoalkanoates which can be used to prepare the thiocarbamates, in ester form, correspond to the formula: HSR'COOR" wherein R" is an alkylene radical generally having from 1 to about 5 carbon atoms and, preferably, from 1 to about 2 carbon atoms and R" is an alkyl radical generally having from 1 to about 10 carbon atoms and, preferably, from 1 to about 5 carbon atoms. The following compounds are illustrative of the alkyl mercaptoalkanoates which can be used to prepare the esters: methyl 2-mercaptoethanoate, methyl 2-mercaptopropanoate, methyl 3-mercaptopropanoate, methyl 5-mercaptopentanoate, ethyl 3-mercaptopropanoate, butyl 3-mercaptopropanoate, hexyl 3-mercaptopropanoate, octyl 3-mercaptopropanoate, decyl 3-mercaptopropanoate and pentyl 4-mercaptobutanoate.

Any suitable inert organic solvent may be used as the environment for the reaction such as benzene, toluene, xylene and the like. The reaction is generally carried out under conditions of agitation and at ambient temperature and pressure.

The interaction of the alkylmercaptoalkanoate with the isocyanate produces a thiocarbamate in ester form which is a crystalline product. This product is separated from the solvent by filtration and is purified by dissolving it in and recrystallizing it from a recrystallization solvent such as a benzene-acetone system.

The aryl thiocarbamates of this invention possess the unique ability of being able to alter or modify biological membranes. A principal physiological effect is that the strength of the biological membrane is apparently enhanced. In particular, it has been found that the erythrocytes of mammals treated with the aryl thiocarbamates of this invention have increased resistance to hemolysis. The thiocarbamates may be administered orally, or by any other suitable technique. The erythrocytes of Swiss-Webster mice, as shown by the examples hereinafter set forth, have substantially increased resistance to hemolysis when their standard daily diet is modified for a period of five to twenty-eight days with the aryl thiocarbamates of this invention at a daily concentration level from about 0.075% to about 0.15%, by weight, based on the weight of the daily diet.

The following examples further illustrate the invention.

EXAMPLE I

This example illustrates a method for preparing 3-(N-paraphenylazophenylthiocarbamoyl)-propanoic acid.

To a one liter flask equipped with a magnetic stirring bar and containing 400 ml of benzene, there is added, sequentially, with stirring, 0.080 mole (8.49 grams, 6.79 ml) of 3-mercaptopropanoic acid and 0.080 mole (8.09 grams, 11.16 ml) of triethylamine to produce a clear solution of a carboxyl blocked, mercaptopropanoic acid, namely, triethylammonium 3-mercaptopropanoate. This salt forming step is completed in about 5 minutes.

To the solution of the ammonium salt, there is added, with stirring, 0.080 mole (17.87 grams) of paraphenylazophenyl isocyanate and the stirring is continued for about ½ hour to produce a thiocarbamate reaction product, namely, triethylammonium 3-(N-paraphenylazophenylthiocarbamoyl)-propanoate. The solvent solution of the thiocarbamate is transferred to a 2 liter separatory funnel and 525 ml of an aqueous solution of sodium bicarbonate, 0.15 N is added thereto to displace the carboxyl blocking group (triethylammonium ion) and to produce sodium 3-(N-paraphenylazophenylthiocarbamoly)-propanoate. The sodium salt is preferentially soluble in the aqueous medium and the aqueous medium is immiscible in benzene. As a result of this immiscibility and differences in specific gravity, the fluid resolves itself into an upper benzene layer and a lower aqueous layer. The aqueous layer containing the sodium salt is separated from benzene. Following the separation step, the aqueous medium is acidified with hydrochloric acid to displace the sodium ion from the thiocarbamate and produce 3-(N-paraphenylazophenylthiocarbamoyl)-propanoic acid which precipitates out of solution as a crystalline product.

The crude product, after being separated from the aqueous medium by filtration, is purified by dissolving it in about 100 ml of hot acetone to which is added about 150 ml of hot benzene. The solution is concentrated by boiling off the solvent until crystalline begins to occur. After crystallization begins, the solution is allowed to cool, slowly at first, and thereafter in an ice bath until the solution reaches a temperature of about 10° C. Upon completion of crystallization, the product is separated from the solvent by filtration. There is obtained about 20 grams of the thiocarbamate in carboxylic acid form. Calculated for $C_{16}H_{15}N_3SO_3$: C, 58.35; H, 4.59; N, 12.76; S, 9.73; Molecular weight 329. Found: C, 58.41; H, 4.49; N, 12.71; S, 9.85; Molecular weight 326. The product melts at 211° C with decomposition.

EXAMPLE II

This example illustrates a method for preparing 2-(N-paraphenylazophenylthiocarbamoyl)-propanoic acid.

Following the procedure set forth in Example I, 0.080 mole (8.49 grams) of 2-mercaptopropanoic acid is sequentially reacted with 0.080 (8.09 grams) mole of triethylamine and 0.080 mole (17.87 grams) of paraphenylazophenyl isocyanate in benzene to produce triethylammonium 2-(N-paraphenylazophenylthiocarbamoyl)-propanoate. 525 ml of 0.15 N sodium bicarbonate solution is added thereto and the resulting aqueous layer containing the sodium salt of the thiocarbamate reaction product is separated from benzene and acidified with hydrochloric acid to produce a crystalline product which is purified by the recrystallization procedure described in Example I.

There is obtained about 20 grams of 2-(N-paraphenylazophenylthiocarbamoyl)-propanoic acid which has a melting point of about 196°–197° C with decomposition.

EXAMPLE III

This example illustrates a method for preparing 2-(N-paraphenylazophenylthiocarbamoyl)-ethanoic acid.

Following the procedure set forth in Example I, 0.080 mole (8.37 grams) of 2-mercaptoethanoic acid is sequentially reacted with 0.080 (8.09 grams) mole of triethylamine and 0.080 mole (17.87 grams) of paraphenylazophenyl isocyanate in benzene to produce triethylammonium 2-(N-paraphenylazophenylthiocarbamoyl)-ethanoate. 525 ml of 0.15 N sodium bicarbonate solution is added thereto and the resulting aqueous layer containing the sodium salt of the thiocarbamate reaction product is separated from benzene and acidified with hydrochloric acid to produce a crystalline product which is purified by the recrystallization procedure described in Example I.

There is obtained about 20 grams of 2-(N-paraphenylazophenylthiocarbamoyl)-ethanoic acid which has a melting point of about 290°–291° C with decomposition.

EXAMPLE IV

This example illustrates a method for preparing 3-(N-metafluorophenyldithiocarbamoyl)-propanoic acid.

Following the procedure set forth in Example I, 0.080 mole (8.49 grams) of 3-mercaptopropanoic acid is sequentially reacted with 0.080 (8.09 grams) mole of triethylamine and 0.080 mole (12.25 grams) of metafluorophenyl isothiocyanate in benzene to produce triethylammonium 3-(N-metafluorophenyldithiocarbamoyl)-propanoate. 525 ml of 0.15 N sodium bicarbonate solution is added thereto and the resulting aqueous layer containing the sodium salt of the thiocarbamate reaction product is separated from benzene and acidified with hydrochloric acid to produce a crystalline product which is purified by the recrystallization procedure described in Example I.

There is obtained about 15 grams of 3-(N-metafluorophenyldithiocarbamoyl)-propanoic acid which has a melting point of about 156°–158° C.

EXAMPLE V

This example illustrates a method for preparing methyl 3-(N-paraphenylazophenylthiocarbamoyl)-propanoate.

To a one liter flask equipped with a magnetic stirring bar and containing 400 ml of benzene, there is added, in sequence, with stirring, 0.080 mole (9.61 grams of methyl 3-mercaptopropanoate and 0.080 mole (17.87 grams) of paraphenylazophenyl isocyanate and stirring is continued for about ½ hour. A crystalline product is formed which is separated from the solvent by filtration and purified by the recrystallization procedure described in Example I.

There is obtained about 20 grams of methyl 3-(N-paraphenylazophenylthiocarbamoyl)-propanoate which has a melting point of about 150°–152° C.

EXAMPLE VI

This example shows that the erythrocytes of mammals treated with 3-(N-paraphenylazophenylthiocarbamoyl)-propanoic acid (Compound A) have increased resistance to hemolysis.

Each of 4 control mice was fed a 4 gram daily allotment of powdered Purina Lab Chow for one week. Each of 3 similar mice was also fed a 4 gram daily allotment of powdered Purina Lab Chow for one week with each daily allotment containing 6 milligrams of Compound A (0.15% of the weight of the daily allotment). After one week, the mice were sacrificed and 20 microliters of blood, from each mouse, was anticoagulated and added, with mixing, to separate tubes holding 5 ml of an isotonic saline solution buffered to a pH of 7.4 and containing 3.25% (w/v) of chloral hydrate. The tubes were placed in a Turner spectrophotometer and the percent transmittance at 620 nm was read at intervals from 1 to 9.5 minutes. The data for all mice in each group was averaged and the results are set forth in Table I.

TABLE I

| Minutes After Blood Addition to Hemolyzing Solution | Control (4 mice) Mean % Transmittance | Treated (3 mice) Mean % Transmittance |
|---|---|---|
| 1" | 29.0 | 30.7 |
| 2" | 37.0 | 34.0 |
| 3" | 63.0 | 42.0 |
| 4" | 90.0 | 50.2 |
| 5" | 97.8 | 59.2 |
| 6" | 98.2 | 68.4 |
| 7" | 98.2 | 73.7 |
| 8" | 98.2 | 76.7 |
| 9" | 98.2 | 77.4 |
| 9.5" | 98.2 | 77.7 |

The data in Table I shows that the induction, rate and degree of hemolysis of mammalian erythrocytes in a chloral hydrate solution in substantially reduced when the mammal is administered 3-(N-paraphenylazophenylthiocarbamoyl)-propanoic acid.

EXAMPLE VII

This example illustrates that various thiocarbamates can be effectively used to increase the resistance of mammalian erythrocytes to hemolysis.

The following thiocarbamates were evaluated:

Compound A
3-(N-paraphenylazophenylthiocarbamoyl)-propanoic acid.
Compound B
2-(N-paraphenylazophenylthiocarbamoyl)-propanoic acid.
Compound C
Methyl 3-(N-paraphenylazophenylthiocarbamoyl)-propanoate.
Compound D
2-(N-paraphenylazophenylthiocarbamoyl)-ethanoic acid.

Each mouse of 5 pairs of mice was fed a 4 gram daily allotment of powdered Purina Lab Chow for 1 week. The first pair was a control group. To the daily allotment of the second, third, fourth and fifth pairs, there was added, respectively, Compound A, Compound B, Compound C and Compound D at a dosage level of 6 milligrams (0.15% of the weight of the daily allotment). Blood samples were treated and evaluated in accordance with the procedure set forth in Example VI. The results are set out in Table II.

TABLE II

Turner spectrophotometer % transmittance at 620 nm,**

| Compd. | Mouse No. | minutes after addition of blood to hemolyzing solution | | | | | | |
|---|---|---|---|---|---|---|---|---|
| | | 1" | 2" | 3" | 4" | 5" | 6" | 7" |
| Control | 1 | 35 | 57 | 98 | 98 | 98 | 98 | 98 |
| | 2* | | | | | | | |
| A | 1 | 33 | 41 | 55 | 76 | 81 | 81 | 81 |
| | 2 | 29 | 36 | 47 | 58 | 72 | 80 | 81 |
| B | 1 | 37 | 64 | 79 | 80 | 80 | 80 | 80 |
| | 2 | 39 | 61 | 74 | 79 | 80 | 80 | 80 |
| C | 1 | 34 | 55 | 84 | 85 | 85 | 85 | 85 |
| | 2 | 34 | 50 | 81 | 90 | 90 | 90 | 90 |
| D | 1 | 46 | 85 | 86 | 86 | 86 | 86 | 86 |
| | 2 | 46 | 73 | 80 | 82 | 82 | 82 | 82 |

*One control animal expired during the experiment.
**96–98% transmittance is complete hemolysis.

EXAMPLE VIII

This example illustrates the use of 3-(N-metafluorophenyldithiocarbamoyl)-propanoic acid (Compound E) to increase the resistance of mammalian erythrocytes to hemolysis.

A control mouse was fed a 4 gram daily allotment of powdered Purina Lab Chow for one week. A second mouse was also fed a 4 gram daily allotment of Purina Lab Chow for 1 week with each daily allotment containing 3 milligrams of Compound E (0.075% of the weight of the daily allotment). After 1 week, the mice were sacrificed and 20 microliters of blood, from each mouse, was anticoagulated and added, with mixing, to separate tubes holding 3.5 ml of a 0.5% acetic acid solution. The tubes were placed in a Beckman DBG recording spectrophotometer and the percent transmittance at 580 mn was continuously recorded for a period of 1 to 12 minutes. The results are set forth in Table III. About 50% transmittance represents complete hemolysis.

TABLE III

Beckman DBG Spectrophotometer % transmittance at 580 mn, minutes after addition of blood to hemolyzing solution

| Compd. | 1" | 2" | 3" | 4" | 5" | 6" | 7" | 8" | 9" | 10" | 11" | 12" |
|---|---|---|---|---|---|---|---|---|---|---|---|---|
| Control | 1 | 5 | 15 | 19 | 24 | 31 | 37 | 44 | 46 | 47 | 47 | 47 |
| Compd. E | 0.5 | 1 | 3 | 6 | 9 | 11 | 13 | 17 | 24 | 32 | 38 | 41 |

EXAMPLE IX

This example shows that mice treated with 3-(N-metafluorophenyldithiocarbamoyl)-propanoic acid (Compound E) have a reduced leucocyte count.

Thirty-two Swiss-Webster mice were divided into 4 groups of 8 mice each. The first group (control group) was fed the standard diet described in Example VI. The second group was fed the standard diet plus 6 milligrams of Compound E. The third group was fed the standard diet plus powdered Datisca root. The fourth group was fed the standard diet plus 6 milligrams of Compound E and powdered Datisca root.

After 18 days of feeding, blood was drawn from all of the animals and leucocyte counts were made using standard counting techniques. The leucocyte counts were (average of 8 mice for each figure, rounded to the nearest 100, per microliter): first group (control) 3,000; second group (Compd. E) 1,400; third group (Datisca) 2,500; and fourth group (Compd. E and Datisca) 700.

Other thiocarbamates which have been found to increase the resistance of mammalian erythrocytes to hemolysis include:

3-(N-phenyldithiocarbamoyl)-propanoic acid.
3-[N-(1-naphthyl)-thiocarbamoyl]-propanoic acid.
3-(N-orthofluorophenylthiocarbamoyl)-propanoic acid.
3-(N-orthochlorophenylthiocarbamoyl)-propanoic acid.
3-(N-metanitrophenylthiocarbamoyl)-propanoic acid.
3-(N-metanitrophenyldithiocarbamoyl)-propanoic acid.
3-(N-paramethylthiophenylthiocarbamoyl)-propanoic acid.
3-(N-2-fluoro-5-nitrophenylthiocarbamoyl)-propanoic acid.

Since the thiocarbamates of this invention produce a blood system in mammals which is unusually resistant to changes in osmotic pressure, these compounds, therefore, are useful in the treatment of hemolytic anemias in which the erythrocytes are easily destroyed by changes in osmotic pressure as, for example, hereditary spherocytosis (also known as congenital hemolytic anemia), hemolytic disease due to Rh incompatibility and to a lesser degree acquired hemolytic anemia, as well as hemolytic anemia due to drugs, to burns, to ABO incompatability, and to elliptocytosis.

In addition to being useful in the treatment of hemolytic anemias, studies have shown that the compounds described herein are useful in the treatment of cell membrane or cell division disorders as in thrombocytopenia, other platelet function disorders and in hemorrhagic diseases involving coagulation deficiencies. Further, studies have shown that these compounds are useful in treating gout, other hyperuricemic disorders, and radiation induced hemorrhage.

EXAMPLE X

This example shows that 3-(N-paraphenylazophenylthiocarbamoyl)-propanoic acid increases the blood platelet count in mammals and, thus, can be useful in the treatment of thrombocytopenic conditions as such occur in various pathological disorders including purpura hemorrhagica, some anemias, rheumatic fever and tuberculosis.

Control mice were fed ground Purina Lab Chow and treated mice were fed 50 mg. of Compound A per 100 grams of ground Purina Lab Chow. Four grams of these diets were allotted per day per mouse. After several treatment periods, groups of mice were sacrificed. Blood samples were collected and diluted using the Unopette No. 5855 system and the platelets were counted in a Neubauer chamber, with the following results:

TABLE IV

| | PLATELET COUNT ($\times 10^6$/ul) | | | | |
|---|---|---|---|---|---|
| Untreated mice | Days on Test Diet | | | | |
| | 7 | 8 | 9 | 16 | 17 |
| 1.075 | 1.572 | 1.278 | 4.018 | 4.780 | 5.275 |
| 1.131 | 2.451 | 2.557 | 4.057 | 4.220 | 4.112 |
| 1.122 | 2.137 | 1.271 | 4.506 | | 4.110 |
| 1.131 | 2.137 | 2.187 | 4.975 | | |
| 1.005 | | | 4.230 | | |
| 1.670 | | | 4.610 | | |
| 0.950 | | | | | |
| 1.362 | | | | | |
| 1.028 | | | | | |
| Mean 1.164 | 2.074 | 1.824 | 4.399 | 4.490 | 4.495 |
| % of Control 100% | 178% | 157% | 378% | 386% | 386% |

EXAMPLE XI

This example shows that 3-(N-paraphenylazophenyl-thiocarbamoyl)-propanoic acid (Compound A) is useful in protecting against and in the treatment of platelet destruction from ionizing irradiation.

Control mice were fed Purina Lab Chow and treated mice were fed 50 mg. of Compound A per 100 grams of Purina Lab Chow. One-half of the mice were X ray irradiated at a 455 roentgen dosage level. (This dosage usually causes death to mice in about 13 days from irradiation time.) In the test procedure, one group of mice was given Compound A food one day before irradiation, a second group of mice was given Compound A food on the day of irradiation and a third group of mice was given Compound A food on the day after irradiation. Eight days after irradiation all the mice were sacrificed. Blood samples were collected and diluted using the Unopette No. 5855 system and the platelets were counted in a Neubauer chamber. The results, expressed as a per cent of the non-irradiated, untreated contol mice were as follows:

TABLE V

| | % |
|---|---|
| Non-irradiated, untreated controls | 100 |
| Irradiated, untreated controls | 22 |
| Comp'd A, one day before irradiation to 8th day | 132 |
| Comp'd A, day of irradiation to 8th day | 155 |
| Comp'd A, one day after irradiation to 8th day | 88 |
| Comp'd A, nine days and not irradiated | 349 |

This example clearly shows that mice fed Compound A before or shortly after irradiation were protected from profound platelet destruction caused by irradiation.

The thiocarbamates described herein can be administered orally, intraperitoneally, rectally, or by other dosage routes and for this purpose they can be formulated, compounded and processed with appropriate additives in accordance with customary pharmaceutical procedures for use in capsule, tablet, liquid or injection form. These compounds can be administered in doses ranging from about 0.05 to about 50.0 mg/Kg depending on the species, size, weight, general health and age of the patient, the route of administration and the rate of absorption from the particular pharmaceutical dosage form.

EXAMPLE XII

This example shows that 3-(N-metafluorophenyldithiocarbamoyl)-propanoic acid (Compound E) increases gaseous exchange in the respiratory system and, thus, is useful in treating respiratory conditions as in asthma and emphysema.

A. (Anoxia). For a period of one week, 4 control mice (Swiss-Webster) were fed 3.5 grams per day of Purina Lab Chow and 4 treated mice (Swiss-Webster) were fed 3.5 grams per day of Purina Lab Chow containing 0.11 wt. % of Compound E. Upon 4 different occasions, a different mouse from each of the control and treated groups was marked for identification and placed in a 500 ml threaded jar which was sealed with a threaded closure. The mice were carefully observed for signs of distress as the oxygen content of the jar became depleted. After 30 minutes, in 3 out of 4 trials, the control mice showed signs of distress as indicated by spasmodic movements from the prone position while the treated mice did not show signs of like distress until 34 to 39 minutes. In the remaining trial, the control and treated mice showed stress in the same time (30 minutes). The increased resistance to anoxia is due to improved gaseous exchange and/or relaxation of bronchial smooth muscle which permits the treated mice to receive or absorb oxygen more efficiently.

B. (Diethyl Ether Anesthesia). The 8 mice used in Part A of this Example were maintained on their same diets for 6 days and then subjected to ether anesthesia. In this procedure, a cotton ball was taped against a small hole drilled in the center of the jar lid. The mice were placed in the jar, the lid secured thereto and 0.75 ml of diethyl ether was pipetted onto the cotton ball. In each case, the mice treated with Compound E became anesthetized first and required longer to recover than the control mice. This example shows a more efficient gaseous exchange or relaxation of smooth muscle which response is similar to that produced by some endogenous compounds such as epinephrine, or some of the prostaglandins which are also known to dilate the bronchi, as well as to have other effects on smooth muscle as well as on inflammation.

That which is claimed is:

1. A thiocarbamate of the formula: RNHCXSR'COOR" wherein
   R is paraphenylazophenyl,
   X is oxygen
   R' is an alkylene radical, and
   R" is hydrogen or an alkyl radical.

2. The compound of claim 1 wherein R' has from 1 to about 5 carbon atoms.

3. The compound of claim 1 wherein R" is an alkyl radical having from 1 to about 10 carbon atoms.

4. The compound of claim 1 wherein the thiocarbamate is 2-(N-paraphenylazophenylthiocarbamoyl)-ethanoic acid.

5. The compound of claim 1 wherein the thiocarbamate is 3-(N-paraphenylazophenylthiocarbamoyl)-propanoic acid.

6. The compound of claim 1 wherein the thiocarbamate is 2-(N-paraphenylazophenylthiocarbamoyl)-propanoic acid.

7. The compound of claim 1 wherein the thiocarbamate is methyl 3-(N-paraphenylazophenylthiocarbamoyl)-propanoate.

8. A method for preparing a thiocarbamate of the formula: RNHCXSR'COOH wherein R is paraphenylazophenyl, X is oxygen, and R' is an alkylene radical, which comprises:
   (1) salifying with an organic base in an inert organic solvent the carboxyl group of a mercaptoalkanoic acid of the formula HSR'COOH, whereby a corresponding carboxyl-blocked mercaptoalkanoate is prepared;
   (2) reacting the carboxyl-blocked mercaptoalkanoate with paraphenylazophenyl isocyanate, a compound of the formula R—N=C=O, whereby a carboxyl-blocked thiocarbamate is obtained; and
   (3) acidifying said carboxyl-blocked thiocarbamate, thereby preparing said thiocarbamate.

9. The method of claim 8 wherein the mercaptoalkanoic acid corresponds to the formula HSR'COOH and R' is an alkylene radical having from 1 to about 5 carbon atoms.

10. The method of claim 9 wherein the mercaptoalkanoic acid is 2-mercaptoethanoic acid.

11. The method of claim 9 wherein the mercaptoalkanoic acid is a 3-mercaptopropanoic acid.

12. The method of claim 9 wherein the mercaptoalkanoic acid is 2-mercaptopropanoic acid.

13. The method of claim 9 wherein the organic base is a tertiary amine.

14. The method of claim 13 wherein the tertiary amine is triethylamine.

15. The method of claim 9 wherein the reactants are interacted in substantially equal molar ratios.

16. The method of claim 13 wherein the treating procedure for removing the tertiary amine carboxyl blocking agent from the thiocarbamate reaction product and obtaining the product in the carboxylic acid form includes the steps of:

adding to the organic solvent solution of the thiocarbamate reaction product an aqueous solution of a water soluble base, which is more basic than the tertiary amine carboxyl blocking agent, to displace the carboxyl blocking agent from the reaction product and to form the salt of the reaction product with the cation of the water soluble base, said salt being preferentially soluble in the aqueous medium which is immiscible in the organic solvent;

separating the aqueous solution of the salt from the organic solvent; and adding a converting acid to the aqueous solution of the salt to obtain the reaction product in carboxylic acid form.

17. The method of claim 16 wherein the water soluble base is an alkali metal hydroxide.

18. The method of claim 16 wherein the water soluble base is an alkali metal carbonate.

19. The method of claim 16 wherein the water soluble base is an alkali metal bicarbonate.

20. The method of claim 17 wherein the alkali metal hydroxide is sodium hydroxide.

21. The method of claim 18 wherein the alkali metal carbonate is sodium carbonate.

22. The method of claim 19 wherein the alkali metal bicarbonate is sodium bicarbonate.

23. The method of claim 16 wherein the converting acid is hydrochloric acid.

24. A method for preparing thiocarbamates corresponding to the formula: RNHCXSR'COOR" wherein R is paraphenylazophenyl, X is oxygen, R' is an alkylene radical and R" is an alkyl radical, which comprises:
   interacting an alkyl mercaptoalkanoate with paraphenylazophenyl isocyanate.

25. The method of claim 24 wherein the interaction is carried out in an inert organic solvent.

26. The method of claim 24 wherein the alkyl mercaptoalkanoate corresponds to the formula HSR'COOR" in which R' is an alkylene radical having from 1 to about 5 carbon atoms and R" is an alkyl radical having from 1 to about 10 carbon atoms.

27. The method of claim 25 wherein the reactants are reacted in substantially equally molar ratios.

28. The method of claim 25 wherein the alkyl mercaptoalkanoate is methyl 3-mercaptopropanoate.

29. A method for increasing the resistance of erythrocytes in a mammal to hemolysis, which comprises:
   systemically administering to said mammal an amount of a thiocarbamate of the formula: RNHCXSR'COOR" wherein
   R is paraphenylazophenyl,
   X is oxygen,
   R' is an alkylene radical having from 1 to about 5 carbon atoms, and R" is an alkyl radical having from 1 to about 10 carbon atoms, effective to increase the resistance of erythrocytes in said mammal to hemolysis.

30. The method of claim 29 wherein the thiocarbamate is 2-(N-paraphenylazophenylthiocarbamoyl)-ethanoic acid.

31. The method of claim 29 wherein the thiocarbamate is 3-(N-paraphenylazophenylthiocarbamoyl)-propanoic acid.

32. The method of claim 29 wherein the thiocarbamate is 2-(N-paraphenylazophenylthiocarbamoyl)-propanoic acid.

33. The method of claim 29 wherein the thiocarbamate is methyl 3-(N-paraphenylazophenylthiocarbamoyl)-propanoate.

34. The method of claim 13 wherein the treating procedure for removing the tertiary amine carboxyl blocking agent from the thiocarbamate reaction product and obtaining the product in the carboxylic acid form includes the steps of:

Adding water to the organic solvent solution of the thiocarbamate reaction product, said reaction product being preferentially soluble in said water which is immiscible in the organic solvent;

separating the water solution of the reaction product from the organic solvent; and adding a converting acid to the water solution of the reaction product to obtain such in carboxylic acid form.

* * * * *